US012599336B2

(12) United States Patent
Zhang et al.

(10) Patent No.: US 12,599,336 B2
(45) Date of Patent: Apr. 14, 2026

(54) WEARABLE APPARATUS FOR CONTINUOUS MONITORING OF PHYSIOLOGICAL PARAMETERS

(71) Applicant: Hong Kong Centre for Cerebro-Cardiovasculer Health Engineering Limited, Hong Kong (CN)

(72) Inventors: Yuanting Zhang, Hong Kong (CN); Zijun Liu, Hong Kong (CN); Nan Ji, Hong Kong (CN); Zhibo Fu, Hong Kong (CN)

( * ) Notice: Subject to any disclaimer, the term of this patent is extended or adjusted under 35 U.S.C. 154(b) by 605 days.

(21) Appl. No.: 18/070,495

(22) Filed: Nov. 29, 2022

(65) Prior Publication Data

US 2024/0023891 A1     Jan. 25, 2024

(30) Foreign Application Priority Data

Jul. 25, 2022     (CN) ......................... 202210880258.X

(51) Int. Cl.
A61B 5/00          (2006.01)
A61B 5/0205       (2006.01)
(Continued)

(52) U.S. Cl.
CPC ............ A61B 5/6815 (2013.01); A61B 5/002 (2013.01); A61B 5/02055 (2013.01);
(Continued)

(58) Field of Classification Search
CPC ... A61B 5/6815; A61B 5/002; A61B 5/02055; A61B 5/02255; A61B 5/1116;
(Continued)

(56) References Cited

U.S. PATENT DOCUMENTS

2014/0140567 A1* 5/2014 LeBoeuf .................. A61B 5/01
381/381
2015/0250418 A1* 9/2015 Ashby ................ A61B 5/02055
600/479
(Continued)

FOREIGN PATENT DOCUMENTS

WO     WO-2016063190 A1 *  4/2016
WO     WO-2020253738 A1 * 12/2020

*Primary Examiner* — Unsu Jung
*Assistant Examiner* — Laura Hodge
(74) *Attorney, Agent, or Firm* — Nevin Carmichael IP

(57)          ABSTRACT

The present invention relates to a wearable apparatus for continuous monitoring of physiological parameters. The invention relates to the field of physiological parameters monitoring technology. The wearable apparatus for the continuous monitoring of physiological parameters comprises an earring body and a monitoring device; wherein the monitoring device comprises a sensor module, the sensor module being arranged at the earring body for obtaining a biological signal at an auricle; the biological signal is to be inputted to a pre-built physiological system model or a deep machine learning model to obtain a physiological parameter; the physiological parameter comprising tonoarteriogram (TAG) signals. The invention realizes the convenience of wearing by a user without affecting normal activities of the user, further allows performing of a long-term monitoring of the user and improving monitoring accuracy while reducing damages to the skin of the ear.

9 Claims, 8 Drawing Sheets

BP: Blood pressure
HR: Heart rate
SpO2: Oxygen saturation
Temp: Temperature

(51) Int. Cl.

| | |
|---|---|
| *A61B 5/022* | (2006.01) |
| *A61B 5/0225* | (2006.01) |
| *A61B 5/0235* | (2006.01) |
| *A61B 5/024* | (2006.01) |
| *A61B 5/11* | (2006.01) |
| *A61B 5/28* | (2021.01) |
| *A61B 5/318* | (2021.01) |

(52) U.S. Cl.
CPC ........ *A61B 5/02255* (2013.01); *A61B 5/1116* (2013.01); *A61B 5/28* (2021.01); *A61B 5/318* (2021.01); *A61B 5/7203* (2013.01); *A61B 5/7225* (2013.01); *A61B 5/7264* (2013.01); *A61B 5/02225* (2013.01); *A61B 5/02241* (2013.01); *A61B 5/0235* (2013.01); *A61B 5/02427* (2013.01); *A61B 5/02438* (2013.01); *A61B 2560/0214* (2013.01); *A61B 2562/0219* (2013.01); *A61B 2562/0247* (2013.01); *A61B 2562/0271* (2013.01); *A61B 2562/04* (2013.01); *A61B 2562/06* (2013.01)

(58) Field of Classification Search
CPC ......... A61B 5/28; A61B 5/318; A61B 5/7203; A61B 5/7225; A61B 5/7264
See application file for complete search history.

(56) References Cited

U.S. PATENT DOCUMENTS

| | | | |
|---|---|---|---|
| 2016/0256117 A1* | 9/2016 | Baik .................... | A61B 5/6803 |
| 2022/0287579 A1* | 9/2022 | Addison ............ | A61B 5/02125 |

* cited by examiner

Pierced Earring                    Magnetic Earring

BP: Blood pressure
HR: Heart rate
SpO2: Oxygen saturation
Temp: Temperature

WEARABLE APPARATUS FOR CONTINUOUS MONITORING OF PHYSIOLOGICAL PARAMETERS

FIELD OF THE INVENTION

The present invention relates to the technical field of physiological parameter monitoring, specifically, the invention relates to wearable apparatus for continuous monitoring of physiological parameters.

BACKGROUND OF THE INVENTION

As people paying more and more attention to the physiological health condition, the application of wearable apparatus is becoming increasingly popular among users, which means that users can monitor and count various physiological parameters in real-time through wearable apparatus, so that they can have an intuitive awareness of the body conditions and then take corresponding measures promptly. However, current wearable apparatus need help with the technical problem of monitoring for a long time while having difficulty ensuring monitoring accuracy.

OBJECTS OF THE INVENTION

An object of the present invention is to provide a wearable apparatus for continuous monitoring of physiological parameters.

The above object is met by the combination of features of the main claims; the sub-claims disclose further advantageous embodiments of the invention.

One skilled in the art will derive from the following description other objects of the invention. Therefore, the foregoing statements of object are not exhaustive and serve merely to illustrate some of the many objects of the present invention.

SUMMARY OF THE INVENTION

The present invention provides a wearable apparatus for continuous monitoring of physiological parameters, which can solve the problem of prolonged monitoring while ensuring high monitoring accuracy.

In one aspect, the present invention provides a wearable apparatus for continuous monitoring of physiological parameters, comprising an earring body and a monitoring device; wherein the monitoring device comprises a sensor module arranged at the earring body for obtaining a biological signal at an auricle; the biological signal is to be inputted into a pre-built physiological system model or a deep machine learning model to obtain a physiological parameter, wherein the physiological parameter comprises tonoarteriogram (TAG) information.

As an optional embodiment, the biological signal described comprises a photoplethysmogram (PPG) signal. The sensor module comprises an optical sensor for obtaining the PPG signal, and the optical sensor is a multi-wavelength PPG sensor.

As an optional embodiment, when the number of the earring body is two, the sensor module comprises an optical sensor and a pressure adjustment component; the optical sensor and the pressure adjustment component are arranged respectively at the two earring bodies; the biological signal comprises a PPG signal and an oscillation signal, the optical sensor being used for obtaining the PPG signal, the pressure adjustment component being adapted to adjust a pressure applied to the auricle to obtain the oscillation signal corresponding to the pressure.

As an optional embodiment, the optical sensor is used for obtaining the PPG signal, the optical sensor being a single-wavelength PPG sensor or a multi-wavelength PPG sensor.

As an optional embodiment, the pressure adjustment component comprises an airbag, a valve, a pressure monitor and an air valve controller, the valve being used for controlling inflation of the airbag, the air valve controller being used for controlling opening and closing of the valve, the pressure monitor being used for controlling a degree of inflation of the airbag to obtain the oscillation signal.

As an optional embodiment, the optical sensor is a reflective optical sensor or a transmissive optical sensor.

As an optional embodiment, the monitoring device further comprises a physiological parameter estimation module for inputting the biological signal into the pre-built physiological system model or the deep machine learning model.

As an optional embodiment, the monitoring device further comprises: a control module arranged at the earring body for controlling the sensor module and performing pre-processing of the obtained biological signal, and for transmitting the pre-processed biological signal to the physiological parameter estimation module; the pre-processing comprises filtering, pre-amplification and noise reduction processing; a communication module arranged at the earring body, wherein when the physiological parameter estimation module is arranged at the earring body, the communication module is used for transmitting the biological signal to the physiological parameter estimation module, and the communication module is used for outputting the physiological parameter obtained by the physiological parameter estimation module; wherein when the physiological parameter estimation module is arranged to separate from the earring body, the communication module is used for transmitting the biological signal to the physiological parameter estimation module.

As an optional embodiment, the biological signal further comprises at least one of a change of body position monitoring signal, an electrocardiogram (ECG) signal, a pressure signal and a temperature signal; the sensor module further comprises at least one of an accelerometer, an ECG electrode, a pressure sensor and a temperature sensor; the accelerometer being used for obtaining the change of body position monitoring signal; the ECG electrode being used for obtaining the ECG signal; the pressure sensor being used for obtaining the pressure signal; the temperature sensor is used for obtaining the temperature signal.

As an optional embodiment, the monitoring device further comprises a power supply module; when the number of the earring body is two, the power supply module comprises two power supply modules and are respectively connected with the two earring bodies; or the power supply module is arranged at one of the earring bodies, and the two earring bodies are connected via a wire.

The technical embodiment of the present invention provides a wearable apparatus for detecting physiological parameters using the earring body placed on the auricle, which is convenient for the user to wear without affecting the user's everyday activities, thus enabling the user to be monitored for a long time. In addition, compared to other parts of the human body, the ear is rich in blood vessels, and the position between the ear and the heart is relatively fixed with less movement, which can improve monitoring accuracy. Also, considering that earrings have a certain degree of stiffness, obtaining the auricular biological signal of the ear reduces the damage to the surface skin of the ear compared to obtaining the external auditory canal biological signal of the ear.

BRIEF DESCRIPTION OF THE DRAWINGS

The foregoing and further features of the present invention will be apparent from the following description of preferred embodiments which are provided by way of example only in connection with the accompanying figures, of which.

DESCRIPTION OF PREFERRED EMBODIMENTS

Embodiments of the present invention are described in connection with the following figures in the present invention. It should be understood that the embodiments set forth below in conjunction with the accompanying figures are exemplary descriptions to explain the technical solutions of the embodiments of the present invention and do not constitute a limitation of the technical solutions of the embodiments of the present invention.

It will be understood by person skilled in the art unless expressly stated, the singular forms "one," "a", "said," and "the" as used herein "may also include the plural form. It should be understood that when we refer to a component being "connected" or "coupled" to another element, the one component may be directly connected or coupled to the other component, or it may refer to the one component and the other component being connected through an intermediate component. The term "and/or" as used herein refers to at least one of the items defined by the term; for example, "A and/or B" may be implemented as "A" or as "B" or "A and B".

In order to make the purposed technical solutions and advantages of this invention clearer, the following will be described in further detail in conjunction with the accompanying figures for the implementation of this invention.

Figure 1:
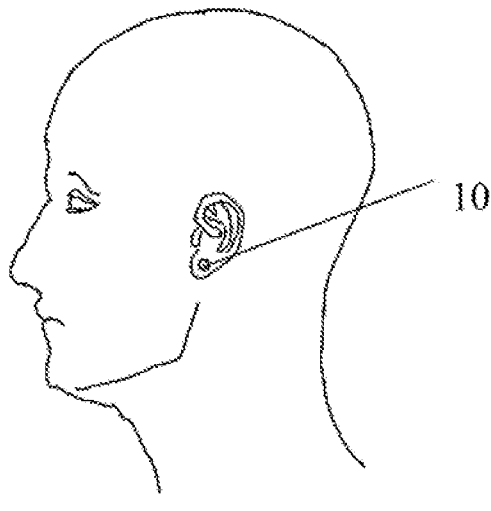
FIG. 1 shows a schematic diagram of the structure of a wearable apparatus for continuous monitoring of physiological parameters provided by embodiments of the present invention.
Figure 2:
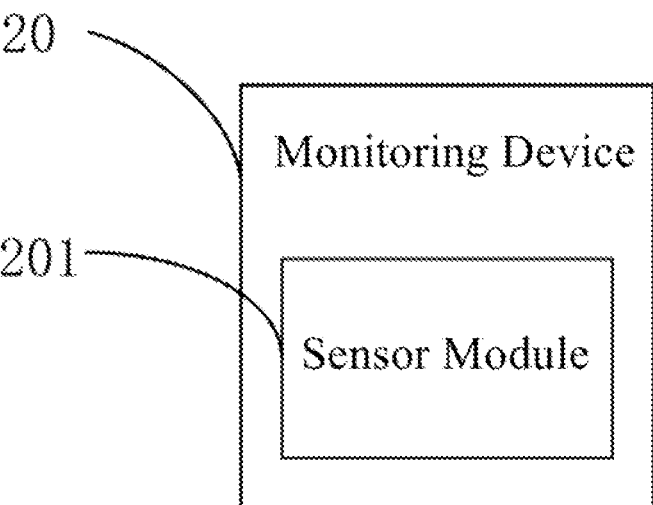
FIG. 2 shows a schematic diagram of the structure of a monitoring device provided by an embodiment of the present invention.

Embodiments of the present invention provide a wearable apparatus for continuously monitoring physiological parameters, as shown in FIGS. 1 and 2. FIG. 1 exemplarily illustrates a schematic structure of a wearable apparatus for continuous monitoring of physiological parameters of an embodiment of the present invention, and FIG. 2 exemplarily illustrates a schematic structure of a monitoring device of an embodiment of the present invention. The wearable apparatus device for continuous monitoring of physiological parameters comprises an earring body 10 and a monitoring device 20.

It can be understood that the earring body 10 is placed on the ear, which is convenient for the user to wear without affecting the everyday activities of the user, so that the user can be monitored for a long time by the monitoring device 20. In addition, compared with other parts of the human body, the ear is rich in vascular distribution and less mobile and relatively fixed position between the heart, which can improve monitoring accuracy, wherein, the monitoring device 20 includes a sensor module 201 provided on the earring body 10, the sensor module 201 is used to obtain the biological signal on the ear, the biological signal will be used to input to a pre-constructed physiological system model or a deep machine learning model to obtain physiological parameters, the physiological parameters include tonoarteriogram (TAG) signals.

In other embodiments, the physiological parameters also include heart rate, blood oxygen, and body temperature.

Considering that earrings have a certain hardness, compared to obtaining biological signal in the external ear canal of the ear, the embodiment of the present invention can reduce the damage to the surface skin of the ear by using the sensor module 201 to collect the biological signal in the ear.

Considering that the user can be monitored for a long time by the earring body 10 placed on the ear, and the tonoarteriogram (TAG) is continuous blood pressure information, compared with the intermittent blood pressure information obtained by devices such as cuffs in the prior art, which only includes systolic blood pressure (SBP) and diastolic blood pressure (DBP), the TAG signal is more accurate in assessing the user's cardio-cerebral vascular system, ensuring the accuracy of the assessment of the user's physical health.

Figure 3:
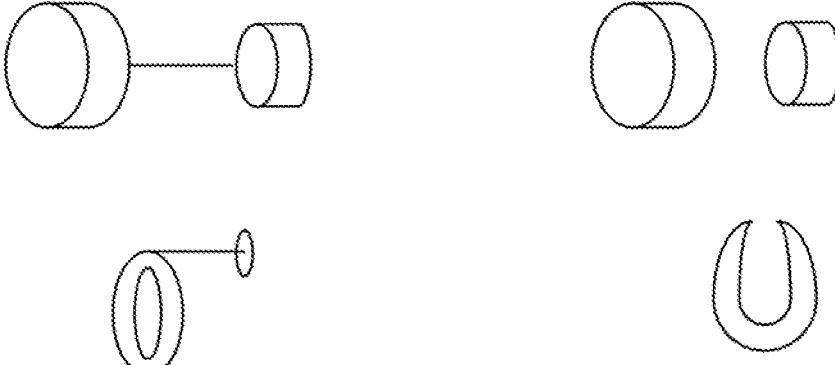
FIG. 3 shows a schematic diagram of the appearance of an earring body provided by an embodiment of the present invention.

Referring to FIG. 3, which exemplarily shows a schematic diagram of the appearance of the earring body of this embodiment, the earring body is either pierced earrings or magnetic earrings to meet the wearing needs of different users, i.e., if the user does not have pierced ears, he/she can use magnetic earrings to achieve wearing, and if the user has pierced ears, he can also choose pierced earrings or magnetic earrings according to his preference. It should be explained that the specific structure and shape of the earring body are not explicitly limited in this embodiment as long as it is easy for the user to wear.

Exemplarily, a deep machine learning model, can be obtained by training in the following manner: first, a certain number of samples are collected, the biological signal of each sample is obtained, and the physiological parameters obtained from the biological signal of each sample are determined, and then, the initial model is trained based on the biological signal of the samples, and the physiological parameters of the samples, wherein the biological signal of the samples is used as the training samples, and the physiological parameters of the samples are used as the sample labels, thereby obtaining a deep machine learning model. The initial model can be a single neural network model or a combination of multiple neural network models.

Based on the above embodiments, as an optional embodiment, the biological signal includes a PPG signal; the sensor module includes an optical sensor, and the optical sensor is a multi-wavelength PPG sensor, i.e., the optical sensor is used to generate multi-wavelength composite light to obtain the MWPPG signal.

It should be explained that the PPG signal, also known as plethysmography signal, is detected by the PPG sensor to obtain the change curve of blood volume over time. Multi-wavelength composite light is light composed of a variety of different wavelengths of monochromatic light, because there are differences in the absorption, attenuation and other effects of blood on each wavelength, so when the optical sensor generates multi-wavelength composite light (i.e., light composed of a variety of different wavelengths of monochromatic light) it can obtain a multi-wavelength PPG (MWPPG) signal. Considering that in order to ensure the accuracy of the physiological system model or deep machine learning model, it is often necessary to input multiple PPG signals into the pre-built physiological system model or deep machine learning model to solve the relevant dependent variable data within the physiological system model or deep machine learning model in order to make the physiological system model or deep machine learning model more adaptable to the user's body condition and thus ensure the accuracy of the physiological parameters when only PPG signals are used to obtain the physiological parameters for the first time. In addition, compared to the prior art by placing additional devices on other body parts of the user to obtain multiple PPG signals, the direct generation of multi-wavelength composite light through the optical sensor 3011 can greatly reduce the number of parts, making the miniaturization of optical sensors conducive to integration and improving the user's experience.

In one embodiment, the biological signal includes a PPG signal and an oscillation signal, and when the number of earring bodies is two, the sensor module includes an optical sensor and a pressure adjustment component, and the optical sensor and the pressure adjustment component are installed on the two earring bodies respectively.

It is understandable that since biological signals include PPG signals and oscillatory signals, the accuracy of the obtained physiological parameters is improved by enriching the variety of biological signals and integrating multimodal biological signals.

It should be explained that the oscillatory signal, also known as pressure pulse waveform graph, is a curve of intravascular pressure over time obtained by applying a certain pressure to the vessel to flatten part of the vessel wall without causing vessel occlusion.

The optical sensor is either a single-wavelength PPG sensor or a multi-wavelength PPG sensor, i.e., the optical sensor is used to generate single-wavelength light or multi-wavelength composite light to obtain a PPG signal. Since the applied pressure can be varied so that multiple oscillation signals can be obtained to calibrate the pre-constructed physiological system model or deep machine learning model, the optical sensor can obtain accurate blood pressure whether it generates single-wavelength light to obtain single-wavelength PPG signals or multi-wavelength composite light to obtain multi-wavelength PPG signals.

Figure 4:
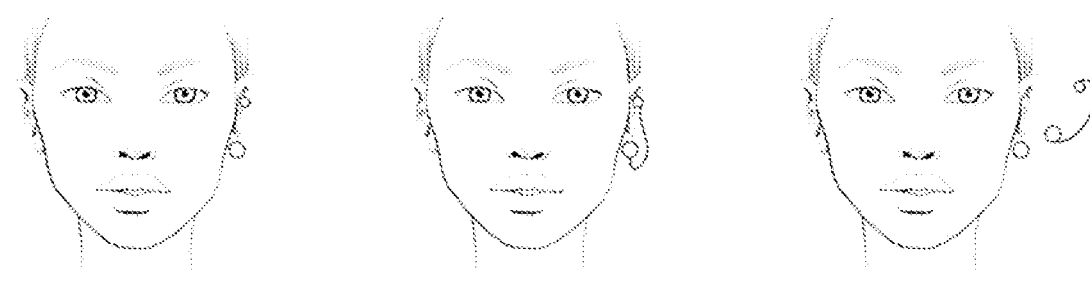
FIG. 4 shows a schematic diagram of the appearance of an earring body provided by an embodiment of the present invention.

Specifically, when the number of earring bodies is two, refer to FIG. 4, which exemplarily illustrates the appearance of an earring body of an embodiment of the present invention, the two earring bodies can be wirelessly connected to each other, thereby facilitating the user to adjust the spacing between the two earring bodies according to preference. Alternatively, in other embodiments, the two earring bodies may be connected by chains or ear hooks to allow the user to store the two earring bodies.

Figure 5:
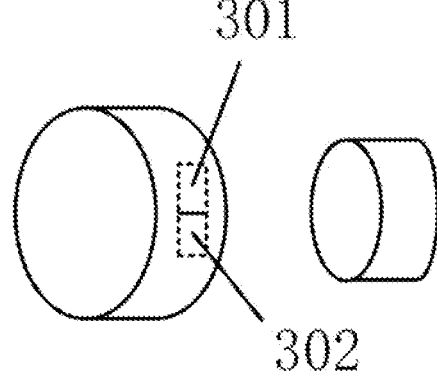
FIG. 5 shows a schematic diagram of the structure of a reflective optical sensor provided by an embodiment of the present invention.

Based on each of the above embodiments, as an optional embodiment, the optical sensor is a reflective optical sensor followed by a transmissive optical sensor. As shown in FIG. 5, which exemplarily illustrates a schematic diagram of the reflective optical sensor of the embodiment of the present invention, the optical sensor includes a light emitter 301 and a photodetector 302. The light emitter 301 and the photodetector 302 in the reflective optical sensor are located on the same side of the ear when the earring body is in contact with the ear auricle, i.e., light is emitted by the light emitter 301 to irradiate onto the ear auricle, and the photodetector 302 is used to receive the light reflected through the skin tissue on the auricle to obtain the PPG signals, the two earring bodies can be connected by chains or hanging ear pieces to allow the user to store the two earring bodies.

As an optional embodiment, in order to be able to adjust the amount of pressure applied to the auricle to obtain an oscillation signal, the pressure adjustment component includes an airbag, a valve, a pressure monitor and a valve controller, i.e., the amount of pressure applied to the auricle is adjusted by the degree of expansion of the airbag, the valve is used to control the expansion of the airbag or not, the valve controller is used to control the opening and closing of the valve, and the pressure monitor is used to control the degree of expansion of the airbag to obtain an oscillation signal.

Figure 6:
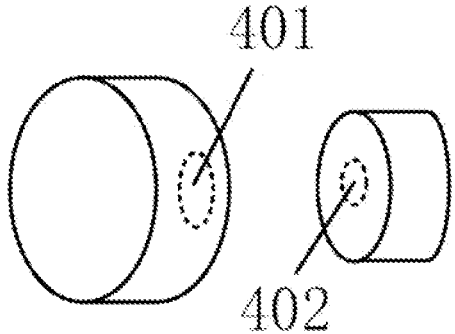
FIG. 6 shows a schematic diagram of the structure of a transmissive optical sensor provided by an embodiment of the present invention.

In other embodiments, as shown in FIG. 6, which exemplarily illustrates a schematic diagram of the transmissive optical sensor of the present embodiment, the earring body is in contact with the ear, the light emitter 401 and the photodetector 402 of the transmissive optical sensor are located on each side of the ear, the light emitter 401 emits light to irradiate onto the ear, and the photodetector 402 is used to receive light after penetrating through the skin tissue on the ear to obtain a PPG signal. The suitability of the earring is further enhanced by the choice of a reflective or transmissive optical sensor.

Based on the above embodiments, as an optional embodiment, the monitoring device further comprises a physiological parameter estimation module, where the physiological parameter estimation module is used to input the biological signal to a pre-constructed physiological system model or a deep learning model.

By integrating a pre-built physiological system model or a deep machine learning model in the physiological parameter estimation module, the response speed can be improved, and the computing efficiency of the monitoring device can be accelerated.

In one embodiment, the physiological parameter estimation module is provided on the earring body to improve the integration of the wearable apparatus for continuous monitoring of physiological parameters. In other embodiments, the physiological parameter estimation module can also be externalized, i.e., set on other wearable apparatus, to further improve the richness of the obtained physiological parameters by interacting with other wearable apparatus.

Based on the above embodiments, as an optional embodiment, the monitoring device further comprises a control module and a communication module; the control module is used to control the sensor module and pre-process the obtained biological signal, and send the pre-processed biological signal to the physiological parameter estimation module, the pre-processing includes filtering, pre-amplification, and noise reduction processing; the communication module is provided on the earring body, and when the physiological parameter estimation module is provided on the earring body, the communication module is used to send the biological signal to the physiological parameter estimation module, and the communication module is used to output the physiological parameters obtained by the physiological parameter estimation module; when the physiological parameter estimation module is set separately from the earring body, the communication module sends the biological signal to the physiological parameter estimation module.

The noise reduction process of the biological signal by the control module is used to reduce the error of the physiological parameters obtained from the physiological system model or the deep machine learning model and improve the physiological parameters' accuracy.

Figure 7:
FIG. 7 shows a schematic diagram of the structure of a wearable apparatus for continuous monitoring of physiological parameters interacting with other wearable apparatus provided by an embodiment of the present invention.

Therein, when the physiological parameter estimation module is provided separately from the earring body, please refer to FIG. 7, which illustrates a schematic diagram of the structure of the wearable apparatus for continuous monitoring of physiological parameters of an embodiment of the present invention interacting with other wearable apparatus, exemplarily including smart bracelets, headphones, rings, and watches, et al.

In one embodiment, the control module includes a controller and a signal processor, the controller is used to control the operation of the sensor module, and the signal processor is used to pre-process the biological signal.

Exemplarily, the signal processor, includes a filter, an amplifier, and an analog-to-digital converter (ADC). The filter is used to filter the biological signal for noise reduction, the amplifier is used to amplify the biological signal for reception by the ADC, and the ADC converts the biological signal into a digital form for input into a physiological system model or a deep machine learning model for computation.

Figure 8:
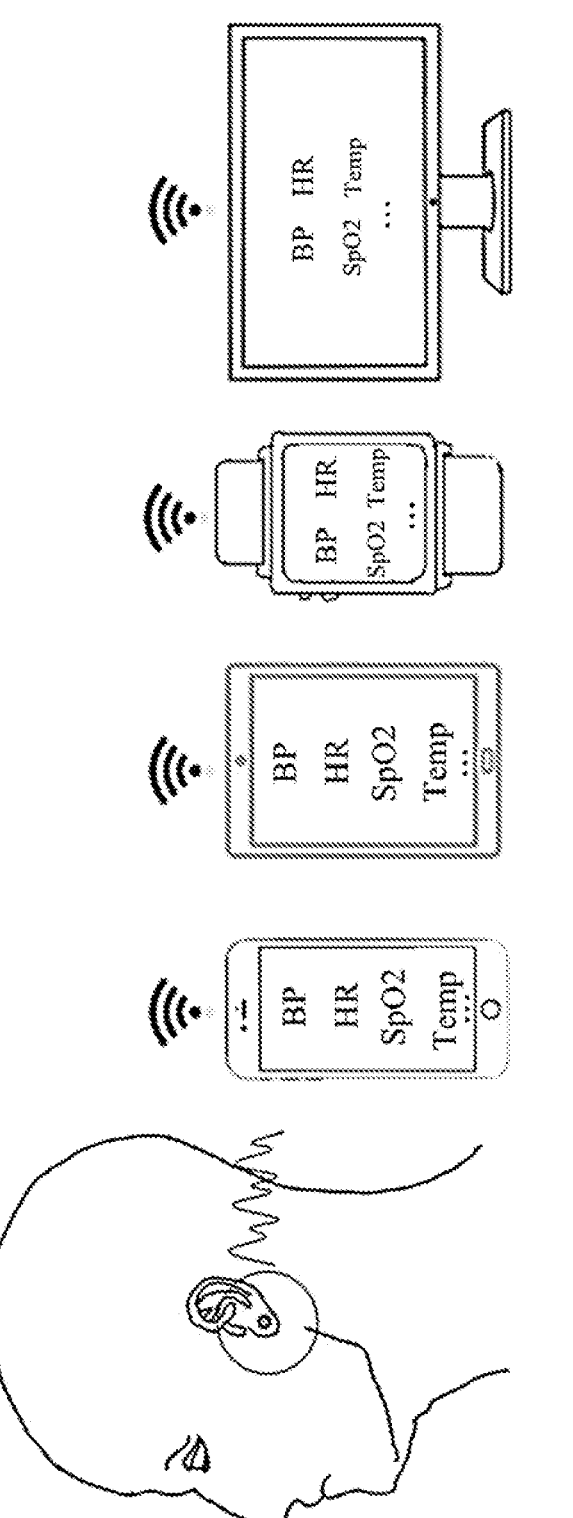
FIG. 8 shows a schematic diagram of a structure of a wearable apparatus for continuous monitoring of physiological parameters provided by an embodiment of the present invention, connected to an external display apparatus.

Exemplarily, referring to FIG. 8, the communication module includes a Bluetooth host for wirelessly connecting with an external display device to output physiological parameters, and the external display device may be a cell phone, tablet, computer, watch, et al.

Based on the above embodiments, as an optional embodiment, the biological signal of this embodiment further includes at least one of a body position change monitoring signal, an ECG signal, a pressure signal and a temperature signal, the sensor module includes an accelerometer sensor, an ECG electrode, a pressure sensor and a temperature sensor, the accelerometer sensor is used to obtain the body position change monitoring signal, the ECG electrode is used to obtain the ECG signal, the pressure sensor is used to obtain the pressure signal and the temperature sensor is used to obtain the temperature signal.

It is necessary to explain that, considering that the physiological parameters obtained from the human body at rest are often more accurate, the postural change monitoring signal obtained can make a judgment on whether the currently obtained PPG signal needs to be input into a physiological system model or a deep machine learning model; similarly, considering that the degree of tightness of the earring body on the ear varies each time it is worn, i.e., the pressure between the earring body and the ear auricle to keep it relatively. The pressure signal obtained from the pressure sensor is used to improve the accuracy of the obtained physiological parameters, considering that the degree of tightness of the earring body on the ear varies each time, i.e., the pressure between the earring body and the ear varies, thus affecting the PPG signal obtained from the optical sensor. The ECG signal obtained by the ECG electrode is faster and more accurate than the heart rate calculated by the PPG signal to improve the efficiency of the obtained physiological parameters.

In an embodiment, to further reduce the number of parts, the infrared light in the multi-wavelength composite light in the optical sensor can also be directly used to obtain the temperature signal instead of the temperature sensor.

Figure 9:
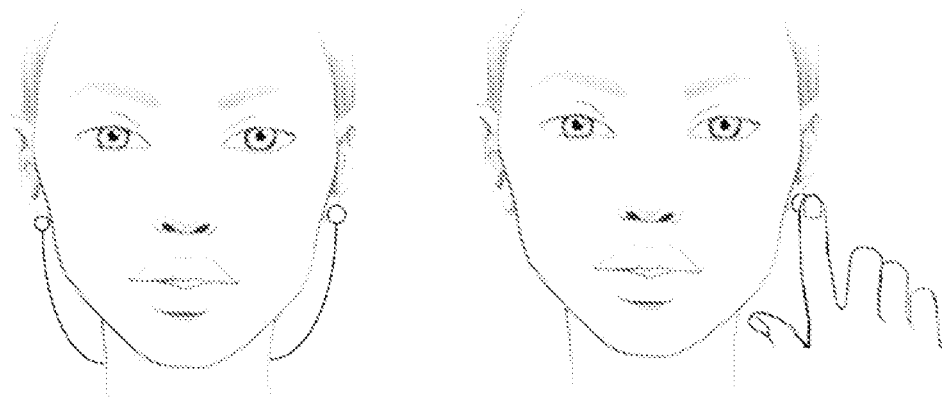
FIG. 9 shows a schematic diagram of the structure of an earring body to obtain an ECG signal, provided by an embodiment of the present invention.

In one embodiment, regarding FIG. 9, which exemplarily illustrates a schematic diagram of the structure of an earring body of an embodiment of the present invention for obtaining an ECG signal, the two earring bodies on the auricle are connected by conductive members to form a conductive pathway to facilitate the ECG electrodes to obtain the ECG signal.

It should be explained that the ECG signal needs to form a conductive pathway between the human body and the earrings to be obtained. If the user wears an earring body on both ears, the conductive pathway can be formed by connecting the earring bodies of both ears with conductive members; however, when the user wears an earring body on only one ear, it is necessary to touch the earring body with the finger of the side not wearing the earring body to form a conductive pathway.

Figure 10:
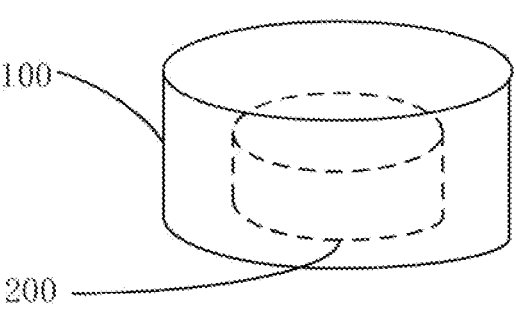
FIG. 10 shows a schematic diagram of the structure of an earring body provided by an embodiment of the present invention.

In one embodiment, reference is made to FIG. 10, which exemplarily shows a schematic structure of the earring body of the present embodiment; the earring body includes a shell 100 with a housing cavity, the monitoring device 200 is placed in the housing cavity, the monitoring device 200 is protected by the shell 100 in all aspects as far as possible, the service life of the monitoring device 200 is prolonged, and the shell 100 is made of conductive material so that a conductive pathway can be formed when contacting the auricle. Optionally, to ensure that the biological signal obtained is as accurate as possible, housing 200 is made of dark-shaded conductive material away from the auricle and the surface near the auricle of transparent conductive material.

Figure 11:
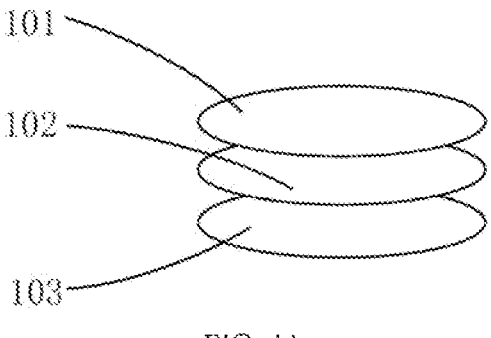
FIG. 11 shows a schematic diagram of a structure of an earring body provided by an embodiment of the present invention.

In other embodiments, referring to FIG. 11, which exemplarily illustrates the structure of the earring body of the present invention; the earring body includes an earring body including a base layer 101, a functional layer 102, and a protective layer 103, the base layer 101 is connected to the ear, and the base layer 101 is made of transparent conductive material, the monitoring device is provided on the functional layer 102, and the protective layer 103 is used to protect the monitoring device to extend the service life of the monitoring device.

Considering that the user wears only one side of the earring body when the ECG signal needs to be obtained, the protective layer 103 may be made of conductive material so that the user touching the earring body can form a conductive pathway.

Based on the above embodiments, as an optional embodiment, the monitoring device also includes a power supply module for providing the power required to monitor physiological parameters for the regular use of the modules in the monitoring device other than the power supply module.

In one embodiment, when the number of earring bodies is two, two power supply modules are provided and connected to each of the two earring bodies; or the power supply module is provided on one of the earring bodies, and the two earring bodies are connected to each other by wires.

It can be understood that if the earring body is wirelessly connected, there are two power supply modules to connect to the two earring bodies one by one; if chains or earpieces connect the two earring bodies, then the power supply module can be set on one of the earring bodies, and the power supply module can supply power to the other earring body by chains or earpieces made of conductive materials (equivalent to wires), or two power supply modules can be set to correspond to the two earring bodies one by one, without any specific limitation in this example.

Figure 12:
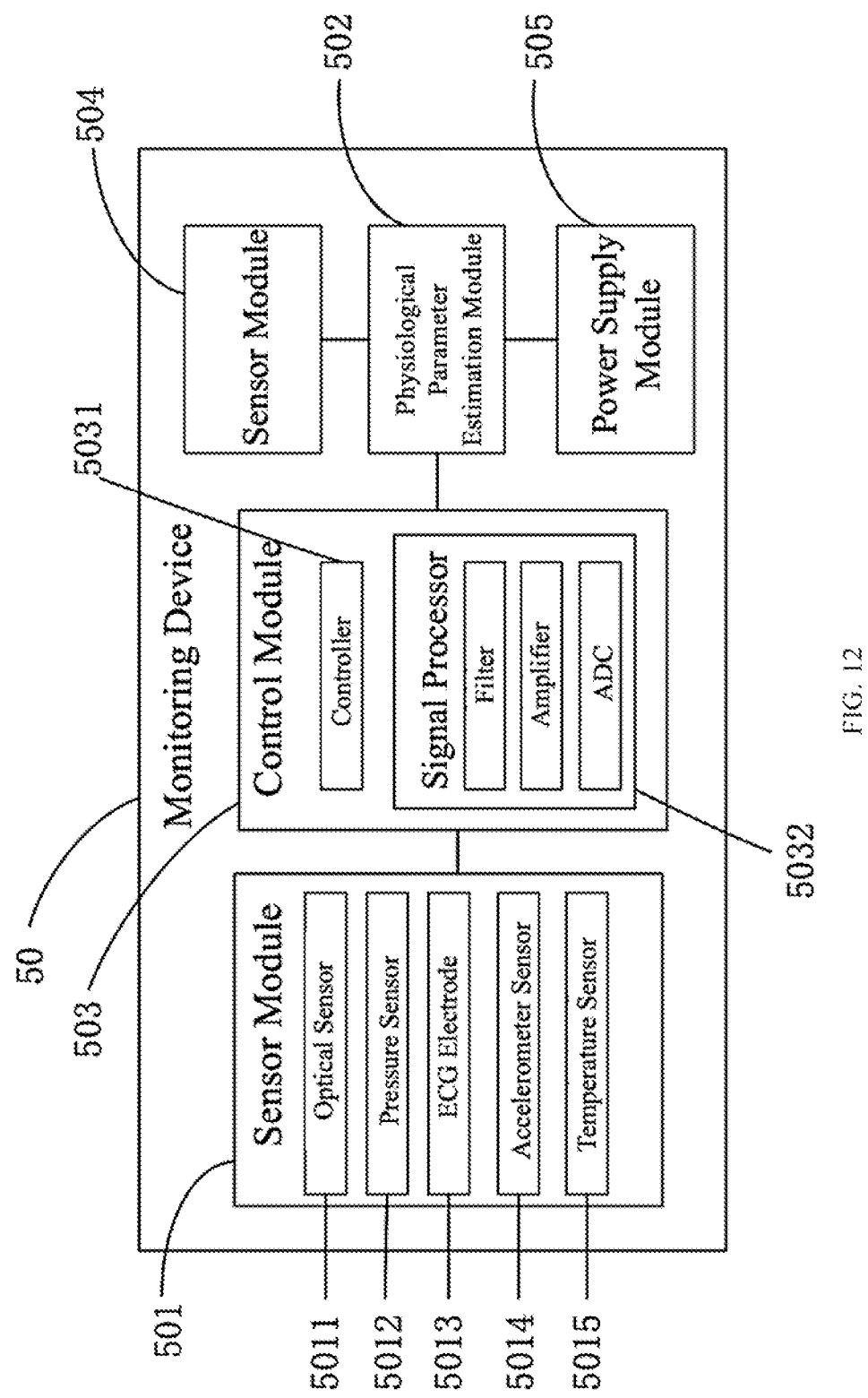
FIG. 12 shows a schematic diagram of a structure of a monitoring device provided by an embodiment of the present invention.

Referring to FIG. 12, which illustrates a schematic diagram of the structure of a monitoring device of an embodiment of the present invention, the monitoring device 50 includes a sensor module 501, a physiological parameter estimation module 502, a control module 503, a communication module 504, and a power supply module 505, the sensor module 501 is used to obtain a biological signal on the ear, the physiological parameter estimation module 502 inputs the biological signal obtained by the sensor module 501 to a pre-constructed physiological system model or a deep machine learning model to obtain a physiological parameter, the control module 503 is used to pre-process the biological signal obtained by the sensor module 501 and send the pre-processed biological signal to a deep machine learning model. The physiological parameter estimation module 502 inputs the biological signal obtained by the sensor module 501 into a pre-constructed physiological system model or a deep machine learning model to obtain physiological parameters, and the control module 503 is used to pre-process the biological signal obtained by the sensor module 501 and send the pre-processed biological signal to the physiological parameter estimation module 502, and the pre-processing includes filtering, pre-amplification, and noise reduction processing; the communication module 504 is used to output the physiological parameters obtained by the physiological parameter estimation module 504 is used to output the physiological parameters obtained by the physiological parameter estimation module 502; the power supply module 505 is used to provide the power required for monitoring the physiological parameters to enable the regular use of the other modules in the monitoring device 50 except the power supply module 505.

The biological signals include PPG signal, body position change monitoring signal, ECG signal, pressure signal and temperature signal. Sensor module 501 includes optical sensor 5011, accelerometer sensor 5014, ECG electrode 5013, pressure sensor 5012 and temperature sensor 5015, optical sensor 5011 is used to obtain PPG signal, accelerometer sensor 5014 is used to obtain body position change monitoring signal, ECG electrode 5013 is used to obtain ECG signal, pressure sensor 5012 is used to obtain pressure signal and temperature sensor 5015 is used to obtain temperature signal.

The control module 503 includes a controller 5031 and a signal processor 5032, wherein the controller 5031 is used to control the operation of the sensor module 501, and the signal processor 5032 is used to pre-process the biological signal.

Exemplarily, the signal processor 5032 includes a filter, an amplifier, and an ADC, where the filter is used to filter the biological signal for noise reduction, the amplifier is used to amplify the biological signal for reception by the ADC, and the ADC converts the biological signal into a digital form for input into a physiological system model or a deep machine learning model for calculation.

Figure 13:
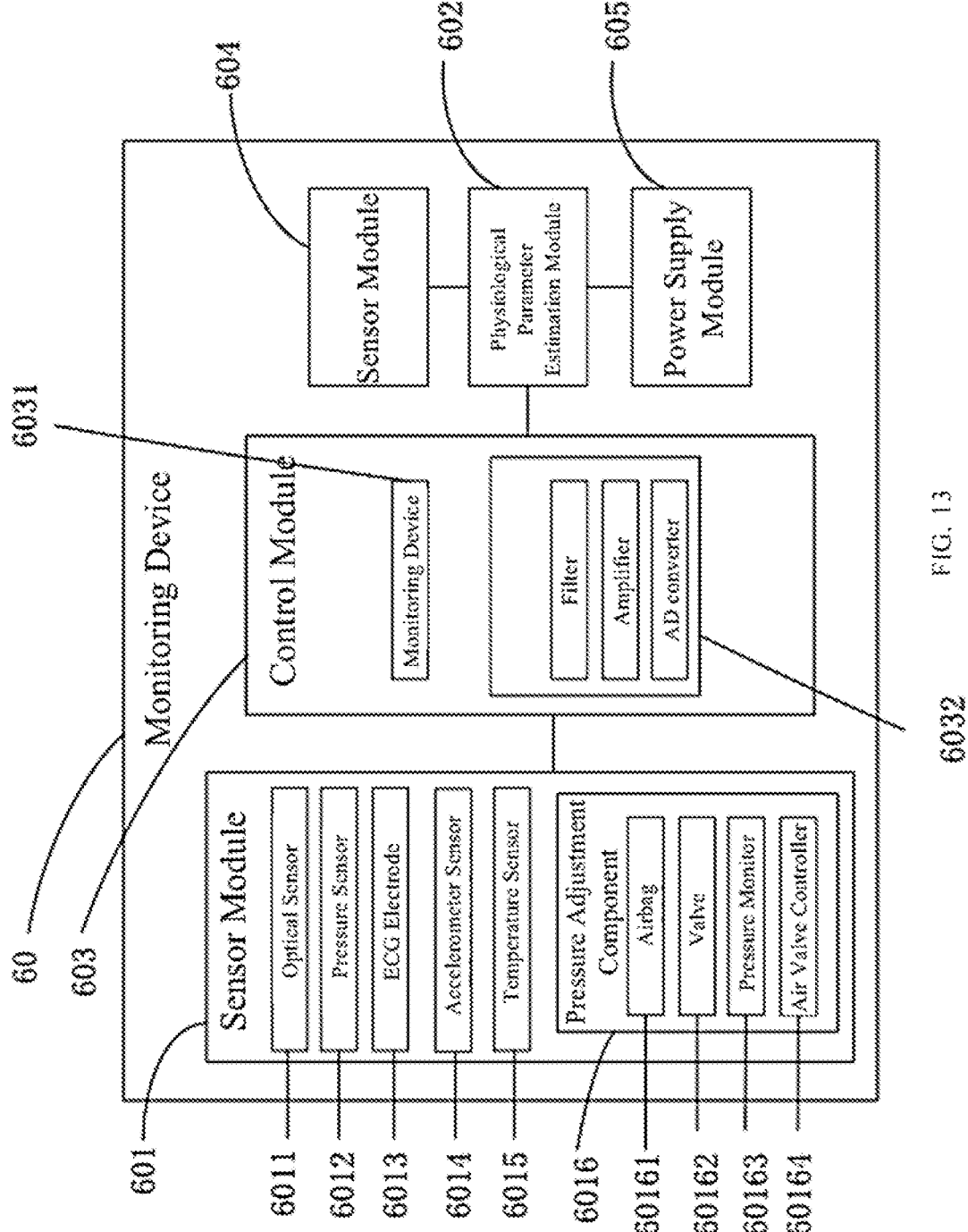
FIG. 13 shows a schematic diagram of the structure of a monitoring device provided by an embodiment of the present invention.

Referring to FIG. 13, which illustrates a schematic diagram of the structure of a monitoring device of an embodiment of the present invention, the monitoring device 60 includes a sensor module 601, a physiological parameter estimation module 602, a control module 603, a communication module 604, and a power supply module 605, the sensor module 601 is used to obtain a biological signal on the ear, the physiological parameter estimation module 602 inputs the biological signal obtained by the sensor module 601 to a pre-constructed physiological system model or a deep machine learning model to obtain a physiological parameter, the control module 603 is used to pre-process the biological signal obtained by the sensor module 601 and send the pre-processed biological signal to a deep machine learning model to obtain a physiological parameter. The physiological parameter estimation module 602 inputs the biological signal obtained from the sensor module 601 into a pre-constructed physiological system model or a deep machine learning model to obtain physiological parameters, and the control module 603 is used to pre-process the biological signal obtained from the sensor module 601 and send the pre-processed biological signal to the physiological parameter estimation module 602, the pre-processing includes noise reduction processing; the communication module 604 is used to output the physiological parameters obtained from the physiological parameter estimation module 602; the power supply module 605 is used to provide the physiological parameters to the sensor module 602. The communication module 604 is used to output the physiological parameters obtained by the physiological parameter estimation module 602; the power supply module 605 is used to provide the power required for monitoring the physiological parameters to enable the regular use of the other modules in the monitoring device 50 except the power supply module 605.

The biological signals include PPG signal, oscillation signal, postural change monitoring signal, ECG signal, pressure signal and temperature signal, and the sensor module 601 includes an optical sensor 6011, a pressure adjustment component 6016, an accelerometer sensor 6014, an ECG electrode 6013, a pressure sensor 6012 and a temperature sensor 6015, the optical sensor 6011 is used to obtain a PPG signal, pressure adjustment component 6016 to obtain an oscillation signal by adjusting the amount of pressure applied to the auricle, accelerometer sensor 6014 to obtain a body position change monitoring signal, ECG electrode 6013 to obtain an ECG signal, pressure sensor 6012 to obtain a pressure signal, and temperature sensor 6015 to obtain a temperature signal.

Exemplarily, the pressure adjustment component 6016 includes an airbag 60161, a valve 60162, a pressure monitor 60163, and a valve controller 60164, i.e., the amount of pressure applied to the auricle is adjusted by the degree of expansion of the airbag 60161, the valve 60162 is used to control the expansion or not of the airbag 60161, the valve controller 60164 is used to control the valve 60162 opening and closing, and the pressure monitor 60164 is used to control the degree of expansion of the airbag 60161 to obtain an oscillation signal.

Among them, the control module 603 includes a controller 6031 and a signal processor 6032, the controller 6031 is used to control the operation or not of the sensor module 601, and the signal processor 6032 is used to pre-process the biological signals.

Exemplarily, the signal processor 6032 includes a filter, an amplifier, and an ADC, the filter for filtering and noise reduction of the biological signal, the amplifier for amplifying the biological signal for reception by the ADC, and the ADC for converting the biological signal into a digital form for input into a physiological system model or a deep machine learning model for computation.

The method of use of this embodiment includes:

obtaining biological signals on the user's ear, including PPG signals, pressure signals, temperature signals, ECG signals, etc., by means of a sensor module;

transmitting the biological signals obtained by the sensor module to the control module and pre-processing them by the signal processor;

inputting the pre-processed biological signals into a physiological system model or a deep machine learning model to obtain physiological parameters, which include TAG information.

In one embodiment, considering that the blood pressure (BP) is formed by the mean blood pressure (MBP) of the stable component and the pulse pressure (PP) of the pulsating component, when the sensor module is not provided with a pressure regulation component, the MBP and PP are obtained first by the biological signal, i.e., the physiological parameters include mean blood pressure and pulse pressure, and the physiological system model includes the following equations:

$$MBP = HR * (k_1 * PTT + b_1)$$

$$PP = MBP * \left(k_2 * \frac{t_r}{HR}\right) + b_2\right)$$

where $k_1$, $k_2$, $b_1$ and $b_2$ are dependent variables, which can be obtained by bringing the signals of multiple PPG signals into the above equation.

Considering that CO=SV*HR, while cardiac output (CO), left ventricular volume per beat (Stroke Volume, SV) and pulse wave transit time (PTT) are obtained from the PPG signal, it is possible to obtain the heart rate (HR).

Considering that the time constant $t_\tau \approx SVR*AC$, and that Peripheral vascular resistance (SVR) and Arterial compliance (AC) can be obtained from the PPG signal, the time constant ($t_\tau$) and diastolic blood pressure (DBP) can be obtained.

Since the physiological parameters also include SBP and DBP, the physiological system model also includes the following equations:

$$DBP = MBP - \frac{1}{3} * PP$$

12

-continued
$$SBP = MBP + \frac{2}{3} * PP$$

Thus, SBP and DBP can be obtained.

In another embodiment, when the sensor module is provided with a pressure adjustment component, the PPG signal changes with the change in pressure because of the deformation of the blood vessels at the pressure site when the applied pressure acts on the user's auricle, so that the blood pressure calibration information can be determined based on the relationship between the PPG signal and the change in pressure, thus avoiding that the PPG signal obtained with only a single wavelength of light is less accurate than the initial blood pressure obtained because it does not include the information about the change in pressure, which affects the user experience.

That is, the above blood pressure detection method includes the steps of obtaining an initial blood pressure, which initial blood pressure is the information obtained by the PPG signal when no pressure is applied by the pressure regulating assembly.

Obtaining a calibrated blood pressure, the calibrated blood pressure being the information obtained by the first pressure of the pressure adjustment component acting on the ear and the PPG signal when that first pressure is applied to the user; calibrating the initial blood pressure based on the blood pressure calibration information and using the calibration blood pressure information as the user's blood pressure.

In this embodiment, considering that a pressure regulation component is provided and that the TAG signal is formed by the maximum pulse amplitude (mean arterial pressure, MAP) and MBP, this embodiment can obtain MAP, DBP, and then SBP indirectly by not applying the technique of characteristic ratio measurement of blood pressure, and obtain MBP by the above equations.

Specifically, the MAP diagram is obtained directly from the relationship between the pressure applied by the pressure regulation component and the supra-auricular vasculature, and the DBP value is obtained based on the highest reduced amplitude in the MAP diagram. The physiological system model includes the following equations:

$$SBP = \frac{1}{\beta} * MAP - \frac{1}{\beta}(1 - \beta) * DBP$$

In turn, the SBP values were obtained, and considering that the physiological parameters also included MBP, the physiological system model also included the following equations:

$$MBP = \frac{1}{3} * SBP + \frac{2}{3} * DBP$$

Thus, the desired MBP is obtained. Where $\beta$ is the systolic ratio of the cardiac cycle, considering that although $\beta$ in the prior art is a fixed value, most of the blood pressure measurements in the prior art are for the brachial artery and not for the ear artery in this embodiment. Therefore, the numerical calculation of $\beta$ is further improved in the present embodiment.

Specifically, in a PPG signal cycle, MAP can be expressed either in discrete or continuous form as follows:

$$MAP = \sum_{i=1}^{n} \frac{p(i)}{n} = \frac{1}{\tau} \int_{0}^{\tau} P(t)dt$$

where the systolic period of blood pressure is $(0, \tau\beta)$, the diastolic period is from $(\tau\beta, \tau)$, and the mean of the total systolic and diastolic pressures (PM) is $$P_M = \frac{1}{\tau} \int_{0}^{\tau\beta} P(t)dt + \int_{\tau\beta}^{\tau} P(t)dt$$

Thus, it is possible to calculate $\beta$ values based on N periods of PPG signals to ensure that the obtained SBP values are more accurate.

The terms "first", "second", "third", "fourth", "1", "2", etc. (if present) in the specification and claims of this invention and the accompanying drawings above are used to distinguish similar objects and need not be used to describe a particular order or sequence. It should be understood that the data so used is interchangeable where appropriate so that the embodiments of the present invention described herein can be implemented in an order other than that illustrated or described in the text.

It should be understood that although arrows indicate the individual operational steps in the flowcharts of embodiments of the present invention, the order in which these steps are performed is not limited to the order indicated by the arrows. Unless explicitly stated herein, in some implementation scenarios of embodiments of the present invention, the implementation steps in the respective flowcharts may be performed in other orders as desired. In addition, some or all of the steps in each flowchart may include multiple sub-steps or stages based on actual implementation scenarios. Some or all of these sub-steps or phases may be executed at the exact moment, and each of these sub-steps or phases may also be executed separately at different moments. In the scenario where the execution time is different, the order of execution of these sub-steps or stages can be flexibly configured according to the needs, and this embodiment is not limited in this regard.

It should be noted that for a person of ordinary skill in the art, other similar means of implementation based on the technical ideas of the present invention, without departing from the technical conception of the scheme of the present invention, also fall within the scope of protection of the embodiments of the present invention.

We claim:

1. A wearable apparatus for continuous detecting physiological parameters of a user wearing the apparatus, comprising:

an earring body and a monitoring device, wherein the monitoring device comprises a sensor module arranged at the earring body for detecting a biological signal at an auricle of the user; and the sensor module comprises an optical sensor; and a pressure adjustment component, wherein the optical sensor comprises a multi-wavelength photoplethysmogram (PPG) sensor adapted to generate a multi-wavelength composite light for detecting a multi-wavelength photoplethysmogram (MWPPG) signal; and the pressure adjustment component is adapted to generate a pressure appliable to the auricle to detect an oscillation signal, and to adjust the pressure to detect multiple oscillation signals; and wherein the biological signal comprising the MWPPG signal and the oscillation signals are processable by a pre-built physiological system model or a deep machine learning model to automatically determine a physiological parameter, wherein the physiological parameter comprises tonoarteriogram (TAG) information.

2. The wearable apparatus for continuous detecting physiological parameters according to claim 1, wherein when the earring body comprises a pair of earring bodies, the optical sensor and the pressure adjustment component are arranged respectively at the pair of earring bodies.

3. The wearable apparatus for continuous detecting physiological parameters according to claim 2, wherein the optical sensor further comprises a single-wavelength PPG sensor.

4. The wearable apparatus for continuous detecting physiological parameters according to claim 1, wherein the pressure adjustment component is selected from the group consisting of an airbag, a valve, a pressure monitor and an air valve controller; wherein the valve is adapted to control inflation of the airbag; the air valve controller is adapted to control opening and closing of the valve; and the pressure monitor is adapted to control a degree of inflation of the airbag to obtain the oscillation signal.

5. The wearable apparatus for continuous detecting physiological parameters according to claim 1, wherein the optical sensor is a reflective optical sensor or a transmissive optical sensor.

6. The wearable apparatus for continuous detecting physiological parameters according to claim 1, wherein the monitoring device further comprises a physiological parameter estimation module for inputting the biological signal into the pre-built physiological system model or the deep machine learning model.

7. The wearable apparatus for continuous detecting physiological parameters according to claim 6, wherein the monitoring device further comprises:

a control module arranged at the earring body for controlling the sensor module and performing pre-processing of the obtained biological signal, and for transmitting the pre-processed biological signal to the physiological parameter estimation module; wherein the pre-processing comprises filtering, pre-amplification and noise reduction processing;

a communication module arranged at the earring body, wherein when the physiological parameter estimation module is arranged at the earring body, the communication module is used for transmitting the biological signal to the physiological parameter estimation module, and for outputting the physiological parameter obtained by the physiological parameter estimation module; and when the physiological parameter estimation module is arranged to separate from the earring body, the communication module is used for transmitting the biological signal to the physiological parameter estimation module.

8. The wearable apparatus for continuous detecting physiological parameters according to claim 1, wherein the biological signal further comprises at least one of a change of body position monitoring signal, an electrocardiogram (ECG) signal, a pressure signal and a temperature signal; and the sensor module further comprises at least one of an accelerometer for obtaining the change of body position monitoring signal, an ECG electrode for obtaining the ECG signal, a pressure sensor for obtaining the pressure signal and a temperature sensor for obtaining the temperature signal.

9. The wearable apparatus for continuous detecting physiological parameters according to claim 1, wherein the monitoring device further comprises a power supply module; when the earring body comprises a pair of earring bodies, the power supply module comprises two power supply modules and are respectively connected with the pair of earring bodies; or the power supply module is arranged at one of the earring bodies, and the pair of earring bodies are connected via a wire.

* * * * *